US009476770B1

(12) United States Patent
Green et al.

(10) Patent No.: US 9,476,770 B1
(45) Date of Patent: Oct. 25, 2016

(54) RESONATOR COUPLING MODULATION SPECTROSCOPY

(71) Applicant: International Business Machines Corporation, Armonk, NY (US)

(72) Inventors: William M. J. Green, Irvington, NY (US); Lionel Tombez, Neuchatel (CH); Eric Zhang, Princeton, NJ (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/008,664

(22) Filed: Jan. 28, 2016

(51) Int. Cl.
*G01N 21/00* (2006.01)
*G01J 3/45* (2006.01)
*G01J 3/42* (2006.01)
*G01N 33/00* (2006.01)

(52) U.S. Cl.
CPC .. *G01J 3/45* (2013.01); *G01J 3/42* (2013.01); *G01N 33/0027* (2013.01)

(58) Field of Classification Search
CPC combination set(s) only.
See application file for complete search history.

(56) References Cited

PUBLICATIONS

Curl, R. F., et al., "Quantum cascade lasers in chemical physics" Chem. Phys. Lett., 1-18, (2010).
De Vos, K. et al., "Multiplexed antibody detection with an array of silicon-on-insulator microring resonators" IEEE Phot. Journal, 225-235, (2009).
Hodgkinson, J., et al. "Optical gas sensing: a review" Meas, Sci, Techn. 24, 012004, 95 Pages (2013).
Kosterev, A. et al., "Application of quantum cascade lasers to trace gas analysis" Appl. Phys. B, 165-176, (2008).
Nitkowski, A., et al. "Cavity-enhanced on-chip absorption spectroscopy using microring resonators" Optics Express, 11930-11936, (2008).
Nitkowski, A., et al. "On-chip spectrophotometry for bioanalysis usingmicroring resonators" Optics Express, 271-277, (2011).
Orghici, R., et al., "A microring resonator sensor for sensitive detection of 1,3,5-Trinitrotoluene (TNT)" Sensors, 6788-6795, (2010).
Robinson, J. T., et al. "On-chip gas detection in silicon optical microcavities," Optics Express, 4296-4301, (2008).
Washburn, A. L., et al. "Label-free quantitation of a cancer biomarker in complex media using silicon photonic microring resonators" Anal. Chem., 9499-9506, (2009).
Yalcin, A., et al., "Optical sensing of biomolecules using microring resonators" IEEE J. Sel. Top. Quant. Elec., 148-155, (2006).
Yariv, A. "Universai relations for coupling of optical power between microresonators and dielectric waveguides" Electron. Lett., 321-322, (2000).

(Continued)

*Primary Examiner* — Tri T Ton
(74) *Attorney, Agent, or Firm* — Cantor Colburn LLP; Vazken Alexanian

(57) ABSTRACT

Disclosed herein is a system for detecting the presence of an chemical in a sample comprising a laser light source for generating a beam of light; a beam splitter that is operative to split the beam of light into a first beam of light and a second beam of light; a reference cell and a first recording device that are operative to receive the first beam of light; where the first recording device is downstream of the reference cell; a resonator that is operative to receive the second beam of light via a coupler; where the resonator contains the sample that contains the chemical; a phase modulator and a second recording device that lie downstream of the resonator and are operative to receive the second beam of light.

20 Claims, 6 Drawing Sheets

(56) References Cited

PUBLICATIONS

Yebo, N. A., et al. "An integrated optic ethanol vapor sensor based on a silicon-on-insulator microring resonator cotaed with a porous ZnO film" Optics Express, 11859-11866, (2010).

Yi, H. et al., "Coupling-induced high-sensitivity silicon microring intensity-based sensor" J. Opt. Soc. Am. B, 1611-1615, (2011).

Yi, H., et al. "Highly sensitive silicon microring resonator with sharp asymmetrical resonance" Optics Express, 2967-2972, (2010).

Sacher, W. D., et al. "Controlled coupling in silicon microrings for high-speed, high extinction ratio, and low chirp modulation" Conference on Lasers and Electro-Optics, PDPA8, (2011) 2 pages.

Green, W. M. J., et al. "Hybrid InGaAsP-InP Mach-Zehnder racetrack resonator for thermooptic switching and coupling control" Optics Express, 1651-1659, (2005).

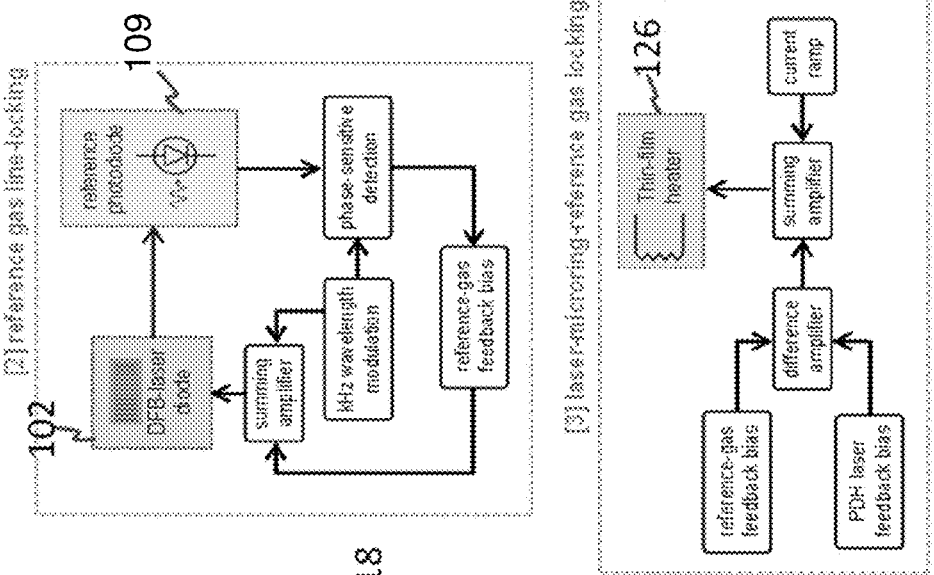
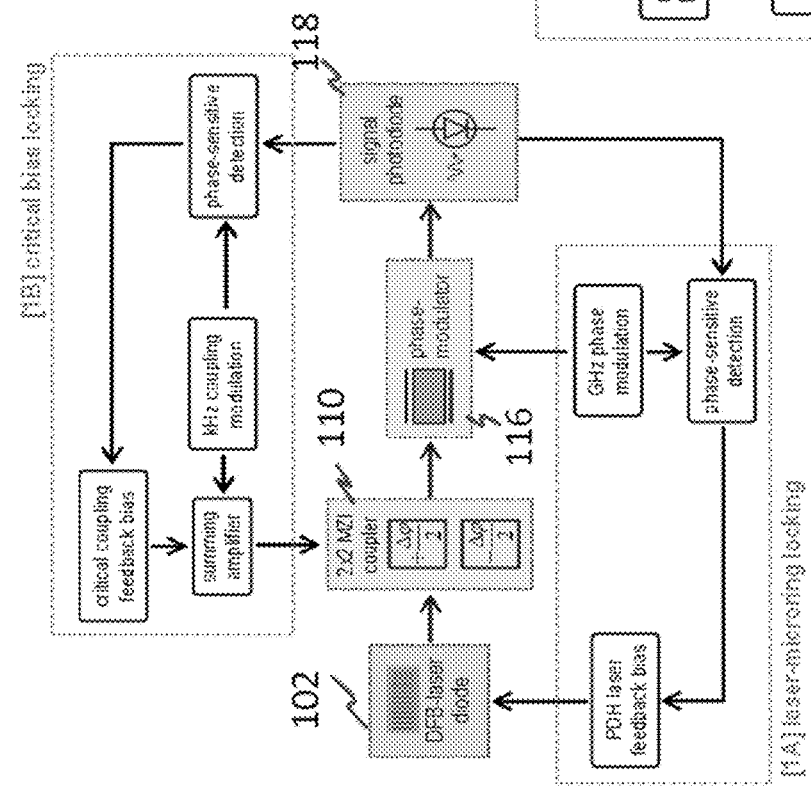
Figure 3(A)
Figure 3(B)
Figure 3(C)

RESONATOR COUPLING MODULATION SPECTROSCOPY

BACKGROUND

This disclosure relates to resonator coupling modulation spectroscopy. In particular, this disclosure relates to resonator coupling modulation spectroscopy for trace-gas analysis.

The increasing analyte selectivity and sensitivity constraints has led to rapid progress in high-resolution spectroscopy. In particular, infrared trace-gas analyzers demonstrate promise as an enabling technology for environmental and medical diagnostics. Mid-infrared (MIR: 3 to 40 μm) and near-infrared (NIR: 0.7 to 3 μm) laser-based spectrometers are widely applicable for sensitive detection due to strong fundamental and harmonic rotational-vibrational transitions in these wavelength regimes. NIR radiation (e.g. 1.65 μm for $2v_3$ overtone-band methane detection) near telecommunication wavelengths is particularly well suited for compact and power efficient spectrometers due to potential for monolithic integration of spectrometer components on a silicon platform.

Numerous spectroscopic schemes have been demonstrated with direct laser-absorption spectroscopy most widely utilized for minimal system complexity. However, in the absence of noise-elimination techniques, the presence of baseline signal fluctuations dominate measurement uncertainty resulting in noise-equivalent absorbance limited by laser technical noise and etalon effects (multiple reflections between two reflecting surfaces). In particular, such problems are exacerbated for on-chip spectrometers due to fabrication tolerances resulting in scattering and optical fringes as well as thermal instabilities resulting in measurement drift. Long-term stability of on-chip sensors have generally remained poor (necessitating frequent spectrometer calibration), and techniques for noise cancellation are lacking. In comparison, free-space techniques utilizing noise reduction (e.g. balanced detection, baseline correction and various modulation schemes) have enabled minimum fractional absorptions below $10^{-5}$ $Hz^{-1/2}$, demonstrating potential of improvement beyond current chip-spectrometer standards.

It is therefore desirable to have a system that resolves the problem of traditional wavelength-modulated etalons (via local modulation of resonant transmission) and low-frequency noise (via kHz coupling modulation rates), while utilizing balanced-detection and resonant enhancement to enable highly-sensitive integrated on-chip tunable laser spectrometers.

SUMMARY

Disclosed herein is a system for detecting the presence of a trace chemical in a sample comprising a laser light source for generating a beam of light; a beam splitter that is operative to split the beam of light into a first beam of light and a second beam of light; a reference cell and a first recording device that are operative to receive the first beam of light; where the first recording device is downstream of the reference cell; a resonator that is operative to receive the second beam of light via a tunable coupler; where the resonator contains the sample that contains the trace chemical; a phase modulator and a second recording device that lie downstream of the resonator and are operative to receive the second beam of light; where the coupler is operative to: a) modulate coupling strength between the resonator and an input waveguide; and b) biasing a coupling between the coupler and the resonator at a critical point; and where an output from the first recording device is compared with an output from the second recording device to determine an amount of the trace chemical.

Disclosed herein is a method for determining concentration of a chemical in a sample comprising splitting an incident beam of light into a first beam of light and a second beam of light; transmitting the first beam of light to a reference cell and a first recording device that is operative to receive the first beam of light; where the first recording device is downstream of the reference cell; transmitting the second beam of light to a phase modulator and a second recording device via a resonator and a coupler; where the resonator contains the sample that contains the chemical; where the coupler is operative to a) modulate coupling strength between the resonator and an input waveguide; and b) biasing a coupling between the coupler and the resonator at a critical point; and comparing an output from the second recording device to that of the first recording device to determine an amount of the trace gas.

BRIEF DESCRIPTION OF THE FIGURES

FIG. 3(A) depicts two exemplary control loops that may be used for laser locking and for critical bias locking;

FIG. 3(B) is an exemplary schematic diagram that depicts an exemplary embodiment of how reference gas line-locking is accomplished;

FIG. 3(C) is an exemplary schematic diagram that depicts an exemplary embodiment showing how the light source is locked to the reference cell and to the resonator;

DETAILED DESCRIPTION

Disclosed herein is a resonantly-enhanced interferometer based on coupling modulation of a resonator for gas spectroscopy. The spectroscopic method disclosed herein is applicable to resonator(s) (also termed cavities) that operate in the optical to terahertz (THz) wavelength range (e.g., visible, ultraviolet, near infrared or mid infrared region) and may be of any desired size. The interferometer can operate at electromagnetic wavelengths of 100 nanometers to 100 micrometers. The size of the resonator can be small (e.g., be disposed on a semiconductor micro-chip) or large (e.g., be in the millimeter range).

In an exemplary embodiment, the resonator is a micro-ring having a diameter of 10 to 1000 micrometers. The design decouples optical etalons using a high quality-factor (Q-factor) resonator, interferometric noise cancellation (balanced-detection) and real-time power normalization. The method comprises splitting an incident beam of light into a first portion that is transmitted into a reference path for line-locking and power normalization while a second portion enters an interferometer that provides coupling to a resonator. The resonator provides enhancement of path length by $F/2\pi$, which results in a large transmission variation in response to coupling variations and ambient gas concentrations. The output intensity is subject to GHz phase modulation for Pound-Drever-Hall (PDH) locking between the laser center frequency and ring resonance. In an exemplary embodiment, the system can be used in the near infra-red range as well as in the mid-infrared wavelength range.

Figure 1:
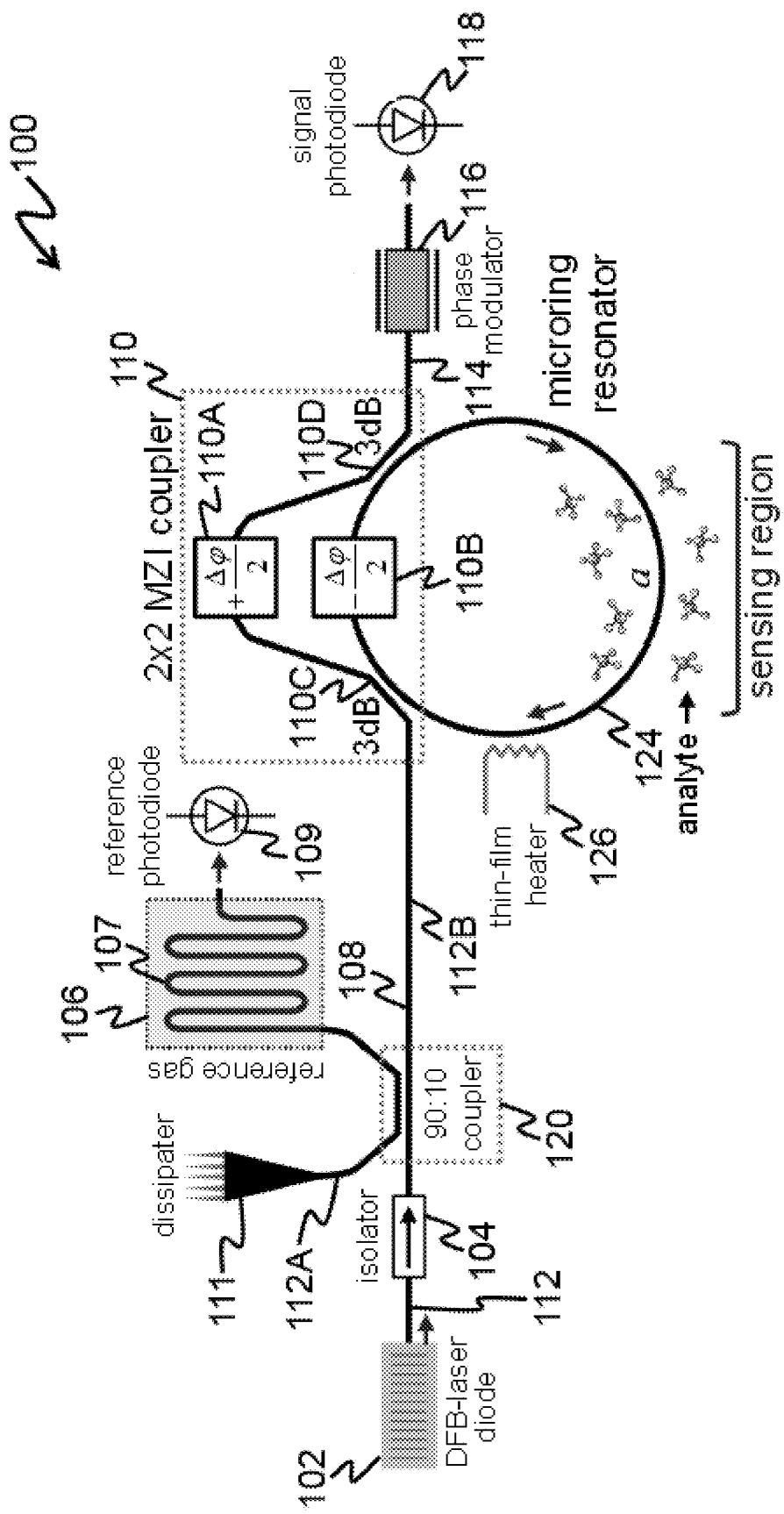
FIG. 1 depicts an exemplary schematic diagram of an exemplary resonantly-enhanced interferometer system 100 that uses coupling modulation to detect trace amounts of a gas.

FIG. 1 is a depiction of an exemplary resonantly-enhanced interferometer system 100 (hereinafter system 100) that uses coupling modulation to detect trace amounts of a first chemical that are contained in one or more other chemicals. In an embodiment, the first chemical and the second chemical are gases. The first chemical can be an element or a compound. The first chemical is also referred to as a trace chemical. The composition being subjected to analysis is also referred to as a "sample". The sample comprises the first chemical distributed in the one or more other chemicals.

In alternative embodiments, the first chemical and the second chemical may be liquids, gases (e.g., aerosols), or solids. The system 100 comprises a source of light 102 from which light emanates to contact a beam splitter 120 where the light is split into a first beam 107 and a second beam 108. In an embodiment, the source of light 102 is a laser source (e.g., a laser cavity) from which light is transmitted to an optical isolator 104 that allows the transmission of light in only one direction. The first beam 107 called the reference beam is transmitted along a first waveguide 112A to a reference cell 106 where it contacts the reference gas and is then discharged to a first recording device 109. The reference cell 106 is also called a reference gas cell. Positioned opposite to the reference cell 106 is a dissipater 111 that prevents unnecessary reflections in the first beam 107.

The second beam 108 is transmitted along a second wave guide 112B to an Mach-Zehnder Interferometer (MZI) coupler 110 that comprises a first 50%/50% (or 3 dB) optical power coupler 110C, a second 50%/50% (or 3 dB) optical power coupler 110D, a first optical phase shifter 110A and a second optical phase shifter 110B. The interferometric coupler 110 is in operative communication with a resonator 124 and couples the incident second beam with the resonator 124. The radiation leaving the resonator 124 is transmitted through an output waveguide 114 to a phase modulator 116 and then to a second recording device 118. Data from the first recording device 109 and the second recording device are then compared to determine gas concentration to which the sensing resonator 124 is exposed. It is to be noted that the first beam 107 and the second beam 108 may be collimated beams of light.

The source of light 102 is a laser source (e.g., a laser cavity) that is in operative communication with the optical isolator 104, the dissipater 111, the reference cell 106 and the first recording device 109 via the first waveguide 112A. The optical isolator 104, the dissipater 111, the reference cell 106 and the first recording device 109 all lie downstream of the source of light 102. In an embodiment, the isolator 104, the beam splitter 120, the coupler 110, the resonator 124, the phase modulator 116 and the second recording device 118 all lie downstream of the source of light 102 and are in operative communication with each other along the second waveguide 112B and the output waveguide 114.

In an embodiment, the "operative communication" is electromagnetic communication and includes communication in the optical and infrared wavelengths. Preferred infrared wavelengths are near infrared (wavelengths of 0.7 to 3 micrometers) and mid-infrared (wavelengths of 3 to 40 micrometers) wavelengths. Details about the respective pieces of equipment in the system 100 are provided below.

In a preferred embodiment, the source of light 102 may be a distributed-feedback (DFB) semiconductor laser diode or vertical cavity surface emitting laser (VCSEL). A distributed feedback laser is a type of laser diode, quantum cascade laser or optical fiber laser where the active region of the device is periodically structured as a diffraction grating. The structure builds a one-dimensional interference grating (Bragg scattering) and the grating provides optical feedback for the laser. Other embodiments may utilize (but are not limited to) fiber-ring lasers, solid-state lasers, gas lasers, chemical lasers and dye lasers.

The optical isolator 104 prevents unwanted feedback into the laser cavity. In an embodiment, the optical isolator 104 may be an optical diode.

In an embodiment, the beam splitter 120 may be a fiber optic coupler with at least one input fiber and at least two output fibers. Light entering the at least one input fiber 112 will appear at the at least two output fibers (112A, 112B) with its power distribution potentially depending on the wavelength and polarization. In an embodiment, the power distribution ratio of the first beam 107 to the second beam 108 varies from 1:99 to 50:50. Generally, more power in the sample path entering 108 is preferred to (i) enhance the signal-to-noise ratio (SNR) near the critical coupling regime and (ii) improve SNR when the sensor operates near the detector or shot-noise limited cases. In short, the second beam 108 is always of a higher power and intensity than the first beam 107, for optimal system operation. In an exemplary embodiment, the power distribution ratio of the first beam 107 to the second beam 108 is 10:90.

The first beam 107 is a reference beam that impinges on a reference cell 106 and then impinges on a first recording device 109. In an embodiment, the reference cell 106 is a high concentration gas cell. The gas cell 106 contains any analyte that the sensor is used to target. In an exemplary embodiment, a semiconductor laser diode operating in the near-infrared targets methane gas (1.65 μm), which has application in environmental monitoring and leak detection. Alternative embodiments utilizing the appropriate source wavelength may be used to target analytes for medical/environmental diagnostics, including but not limited to the near infrared (NIR): ammonia (1.53 μm), carbon dioxide (1.6 μm), carbon monoxide (1.58 μm) and hydrogen sulfide (1.58 μm), and mid-infrared (MIR): nitrous oxide (5.4 μm), nitrogen dioxide (6.2 μm), formaldehyde (3.5 μm), benzene (5.1 μm), nitric oxide (5.4 μm), ethane (3.3 μm).

In an embodiment, the first recording device 109 is a reference photodiode that collects absorption data about the absorption of the first beam 107 by the concentrated gas present in the reference cell 106. This absorption data is then compared with the absorption data collected from the second beam 108 that will be detailed later. The comparison enables identification and concentration information about the first and the second chemicals present in the resonator 124. The first recording device 109 also utilizes first beam 107 as a wavelength reference for operation in the line-locked mode via wavelength modulation of source 102 (wavelength modulation spectroscopy).

The path of the first beam 107 of light (also called the reference path) is used for wavelength referencing using a PID (proportional-integral-derivative) control loop and standard wavelength modulation of the laser that operates in the kilohertz regime. Preferred frequencies in the kilohertz regime are 1 to 1000 kilohertz, where the exact frequency of modulation may be chosen such that the relative etalon strengths are minimized with respect to the wavelength modulated reference spectrum (i.e. third harmonic demodulated via phase sensitive detection). Disposed at the opposite end of the beam splitter 120 is the dissipater 111, which ensures that any detector facet light reflections are largely eliminated.

The second beam 108, which is of a higher power than the first beam 107, is fed into an interferometric coupler 110 via the second waveguide 112B (also referred to herein as an input waveguide since it inputs radiation into the resonator 124). The interferometric coupler 110 is composed of two optical phase shifters 110A and 110B with variable phase shifts (push-pull configuration) to tune power coupling between the resonator 124 and an output waveguide 114. The output waveguide 114 outputs the resulting interferometric radiation from the resonator 124 and coupler 110. In an exemplary embodiment, the first coupler 110C and the second coupler 110D are 3 decibel (dB) couplers. The coupler-resonator combination provides an enhancement of the resonator's physical path length (circumference of 124) by $F/2\pi$ (where F is the resonator finesse), which results in a large transmission variation in response to coupling variations and small changes in the absorbing ambient gas concentrations.

The coupler 110 is biased at the critical coupling point for null optical throughput (i.e., the coupler setpoint at which all incident light in the waveguide 112B enters the resonator 124 and no light passes through to the output waveguide 114), and the coupler is modulated at kHz levels for low-frequency noise reduction. By tracking the critical coupling point while maintaining constant modulation depth, the throughput intensity probes the under-coupled regime where the fractional intensity variation is greatest. The critical coupling point is defined to occur when the output light into waveguide 114 undergoes complete destructive interference, and occurs when the round trip field loss of the micro-ring is equal to the transmission coefficient of coupler 110. Maintaining the constant coupling modulation depth ensures that the coupling 'swing' is the same, thereby causing a relative transmission variation as the analyte concentration changes the resonator's round trip field loss and consequently its critical coupling point. Probing the under-coupled regime (the steep slope in the inset of FIG. 6(A)) allows SNR enhancement by the resonant enhancement factor due to the presence of a high-quality factor micro-ring.

The resulting modulated optical signal is demodulated via phase-sensitive detection. In an embodiment, the coupler 110 is a Mach-Zehnder interferometric coupler. The Mach-Zehnder interferometric coupler is a coupler that produces controlled relative phase shift variations between the two beams 110A and 110B. The coupling coefficient is determined by phase shift in the two arms of the MZI, and this is matched with the round trip field loss to maintain the system at critical coupling. In an alternative embodiment, the coupler 110 may be a micro-electro-mechanical system (MEMS) tunable optical directional coupler, wherein the MEMS device controls (via an electrical bias) the physical separation and/or the physical coupling length between the input waveguide 112B and the optical resonator 124 and thus controls the magnitude of optical coupling between the waveguide and the resonator. In an alternative embodiment, the coupler 110 may be an electro-optic device which can control the refractive indices of the waveguide 112B, the resonator 124, or the cladding material surrounding either (via an electrical bias), and thus controls the magnitude of optical coupling between the waveguide and the resonator. Tracking of the critical coupling can enable an operator to determine changes in the round trip cavity loss, which is a direct reflection of the concentration of analyte introduced to the resonator 124. This change in the coupling coefficient can be used in conjunction with thermal resonance tuning and high-frequency phase modulation to determine compositions of trace gases. The thermal resonance tuning and high frequency phase modulation are detailed below.

The resonator 124 is a device or system that exhibits resonance or resonant behavior, that is, it naturally oscillates at some frequencies, called its resonant frequencies, with greater amplitude than at others. In an embodiment, the resonator 124 is a cavity resonator, which is a hollow closed conductor such as a metal box or a cavity within a metal block, containing electromagnetic waves (radio waves) reflecting back and forth between the cavity's walls. When a source of electromagnetic radiation at one of the cavity's resonant frequencies is applied, the oppositely-moving waves form standing waves, and the cavity stores electromagnetic energy. Due to the low resistance of their conductive walls, cavity resonators have very high Q factors; that is their bandwidth, the range of frequencies around the resonant frequency at which they will resonate, is very narrow. Thus they can act as narrow bandpass filters.

In an embodiment, the resonator 124 is a ring resonator, preferably a micro-ring resonator. An optical ring resonator comprises one or more waveguides in which at least one is a closed loop coupled to some sort of light input and output. When light of a resonant wavelength is passed through the loop from input waveguide 112B, it builds up in intensity over multiple round-trips due to constructive interference and is output to the output waveguide 114 which serves as a detector waveguide that is in communication with the second recording device 118. Because only a select few wavelengths will be at resonance within the loop, the optical ring resonator functions as a filter.

In an embodiment, the resonator 124 cavity may have an integrated heater element for thermal control (not shown) disposed on an inner surface of the cavity wall. The integrated heater may generally comprise a metal such as silicon or a combination of another metal with silicon (e.g., a silicide). The integrated heater element in FIG. 1 is a thin film heater 126 (detailed below), and changing the temperature of the resonator can be used to tune the cavity—i.e., shift its resonance to desired values. In an embodiment, by changing the resonator temperature the resonant frequency of the cavity can be changed. In some embodiments, the thin film heater 126 is a resistive heater and uses electricity for heating the resonator 124 cavity. Changing the temperature of the resonator 124 and the coupler 110 permits the resonant frequencies in the cavity to be changed to desired values. In other words, the thin film heater 126 can be used to tune the resonator 124 cavity. This mode of tuning the resonator is called thermal resonance tuning and is discussed in detail below in the FIG. 3.

When the second beam 108 of light passes through the input waveguide 112B as shown in the FIG. 1, part of light will be coupled into the resonator 124 because of the transmission effect. In other words, when the resonator 124 and the waveguide 112B are coupled via a non-zero power coupling set point of the Mach-Zehnder coupler 110, light in the waveguide will be partially transmitted into the resonator 124.

Downstream of the resonator 124 is an electro-optic phase modulator 116 for locking of the laser beam center frequency to the cavity resonance frequency. In an embodiment, the locking of the laser center frequency is accomplished by Pound-Drever-Hall (PDH) locking. Frequency stabilization is needed because all lasers demonstrate frequency drift at some level. This instability is primarily due to temperature variations, mechanical imperfections, and laser gain dynamics, which change laser cavity lengths, laser driver current and voltage fluctuations, and many other factors. PDH locking offers one possible solution to this problem by actively tuning the laser to match the resonance condition of the cavity.

Using PDH locking, in one embodiment, light from the resonator output 114 is phase modulated at gigahertz rates by 116, enabling fast locking via demodulation and laser current feedback. This feedback may be used simultaneously with critical bias locking (coupling modulation at kilohertz rates via 110A and 110B) to enable concurrent laser-microring wavelength locking and critical coupling bias locking. The PDH feedback loop is completed using a PDH servo that produces a laser bias offset based on the PDH error signal readout and converts it into a voltage that can be fed back to the laser light source 102 to keep it locked on resonance with the resonator 124 cavity. The critical-coupling bias locking loop is completed by a PID servo that produces a coupling bias feedback based on odd-harmonic demodulation of the resulting kilohertz amplitude modulation of the CMS signal on photodiode 118 feedback.

High-frequency phase-modulation beyond the resonance linewidth results in sidebands well outside of the coupling-modulated (CM) intensity change, causing only the desired carrier to experience amplitude modulated coupling-modulated spectroscopy (CMS) signals. Care must be taken that the modulation frequency does not coincide with the cavity free-spectral range (which would induce crosstalk between resonances). The electronic feedback control schemes are outlined in FIG. 2, and a feedback control flow-chart is provided in the FIG. 4, both of which are discussed below.

Figure 2:
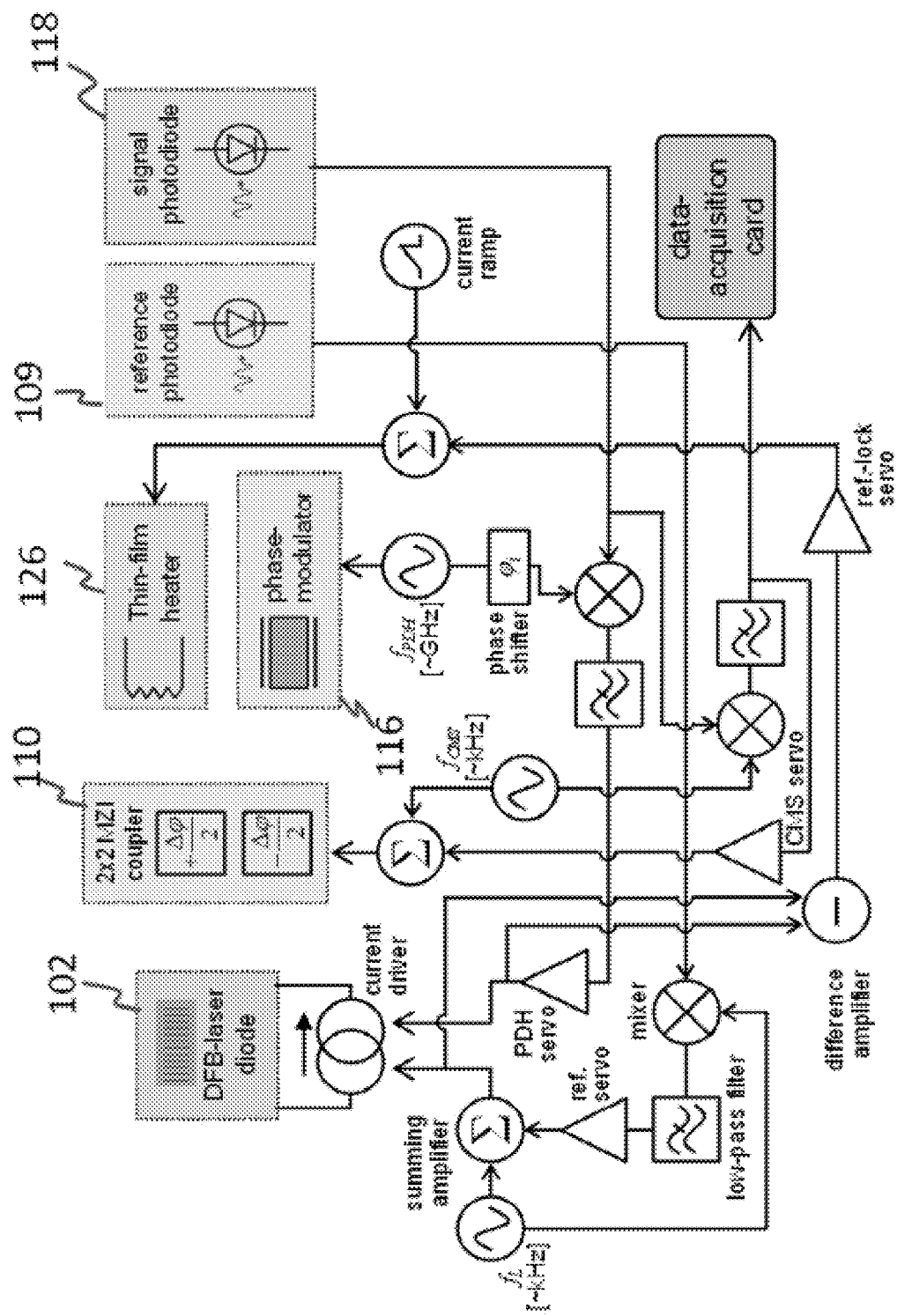
FIG. 2 is a schematic depiction of the feedback control electronics in the system.

FIG. 2 is a schematic depiction of the feedback control electronics in the system 100. As detailed above, PDH locking is accomplished by high-frequency (MHz to GHz) phase modulation 116 of the transmitted signal intensity and measured on the second recording device 118. The PDH feedback locks the laser 102 center frequency to the resonant frequency of the resonator 124. The resonator 124 frequency and hence the wavelength is controlled via thermal resonance tuning by the thin film thermal heater 126 and can be either scanned or locked to that recorded by the first recording device 109. As noted above, the first recording device 109 and the second recording device 118 can both be photodiodes. In an embodiment, the photodiode 109 measures the reference gas spectra, which indicates the laser bias used to provide correct output wavelength, while photodiode 118 determines the offset between the laser wavelength and the peak of the resonator filter function, which in line-locked mode is compensated via feedback control loop 3 in the FIG. 3C for thermal resonance tuning of resonator 124 via heater element 126. Once laser, cavity and reference-locking are accomplished, the resonator coupling 110 is modulated at kHz levels and demodulated directly from the signal photodiode 118 for CMS spectral retrieval.

FIGS. 3(A), 3(B) and 3(C) depict four feedback control loops. FIG. 3(A) depicts two exemplary control loops that may be used for laser locking and for critical bias locking. Control loop 1A is used for laser locking while control loop 1B is used for critical bias locking. In the loop 1A, information about the phase modulation from the phase modulator 116 and phase sensitive detection information from the second recording device 118 (e.g., a photodiode) via PDH feedback may be used to vary the voltage to the light source 102 to lock the laser at the resonant frequency of the resonator 124. The first feedback control loop 1A thus uses phase modulation information from the phase modulator and phase-sensitive detection information from the second recording device to lock a central frequency of the laser light source to a resonant frequency of the resonator.

In the loop 1B, critical bias coupling locks the coupler to the critical coupling point for null optical throughput, which tracks the ambient absorption and provides spectral signals. The second feedback control loop 1B uses phase-sensitive detection information from the second recording device and coupling modulation information from the coupler to determine critical point (bias) coupling between the coupler and the resonator.

The FIG. 3(B) depicts an exemplary embodiment showing how reference gas line-locking is accomplished. Here the reference-gas feedback bias from the reference cell 106 (See FIG. 1) is coupled with phase-sensitive detection information obtained from the second recording device 118 (e.g., a photodiode) to lock the laser center wavelength to the reference gas resonance. The FIG. 3(C) depicts an exemplary embodiment showing how the light source 102 is locked to the reference cell 106 and to the resonator 124. Here the reference gas feedback bias from the reference cell 106 is coupled with the PDH feedback from the second recording device (e.g., a photodiode) 118 and the phase modulator 116 to determine how much current is supplied to the thin film heater 126 which is in communication with the resonator 124 (See FIG. 1). By varying the current to the thin film heater 126, the resonant frequency can be changed. In this manner, the resonant frequency in the cavity can be locked to the laser light source 102 and to the reference cell 106. In an embodiment, the feedback loop of the FIG. 3(B) can be time-multiplexed with the feedback loop of the FIG. 3(C) to thermally bias the resonator at the peak absorption of the sample that is introduced into the resonator 124. The resonance in the resonator is enhanced by time-multiplexing between small and large amplitude coupling modulation. Small amplitude modulation enables lock-bias at the critical point, and large amplitude modulation probes the under-coupled regime, which provides the resonant enhancement factor of the cavity.

Among the feedback locking loops outlined above, it is to be noted that the feedback loop [1A] and the feedback loop [1B] are independent of each other but may be concurrently used without interference as seen in the FIG. 3(A). These two feedback loops may be used either sequentially or simultaneously to facilitate trace gas identification. In an embodiment, the two feedback loops are used simultaneously.

Furthermore, within the constraints of feedback control schemes described in FIGS. 3(A) through 3(C), the system 100 may be deployed in at least two different measurement approaches for sensing the presence of a first gas that is present in a trace amount in a second gas or multi-component gas mixture. In an embodiment, the feedback loops [1A] and [1B] in FIG. 3(A) are sequentially or simultaneously used with each other along with the feedback control loops of the FIGS. 3(B) and 3(C). The feedback control loops of the FIGS. 3(B) and 3(C) are used intermittently to ensure the thermal bias is coarsely centered on the absorption line of interest, while current to the light source 102 is varied to enable a full spectral sweep of the cavity resonance. If traces of the first chemical are present in a sample contained in the resonator 124, then absorption by the first chemical will be detected and its presence identified. This mode of operating the system 100 is called the line scanning mode.

In another embodiment termed the line locking mode, the feedback loops [1A] and [1B] in FIG. 3(A) are simultaneously used and time-multiplexed with the feedback control loops of the FIGS. 3(B) and 3(C) to ensure that the resonator frequency and the absorption line of a gas present in the resonator are wavelength-synchronized. The ramp is turned off to continuously probe only the peak absorption signal.

In each of the above cases (i.e., the line scanning mode and the line locking mode), spectral and concentration retrieval may be accomplished in two different methods. In the first method, termed the critical-bias coupling lock, the kHz-rate coupling modulation and phase-sensitive detection will enable precise locking to the critical coupling point for null optical throughput. This critical point will move in accordance with the concentration of the first chemical (e.g., the trace gas concentration in the gas sample present in the resonator).

In the second method termed critical-bias coupling lock with resonant enhancement, kHz-coupling modulation rates are again used, however small- and large-amplitude modulations are alternated through the resonator 124. Small amplitude modulation is used for critical-coupling bias determination and large amplitude modulation probes the under-coupled regime for resonantly enhanced signals.

The principal benefit of using critical-bias coupling lock with resonant enhancement over only the critical-bias coupling lock is the reduction of drift associated with long-term measurements. For example, the critical coupling point may remain fixed, yet the bias voltage changes to maintain the same coupling to compensate for slow thermal drifts.

By combining the a) line scanning mode and the b) line locking mode with the c) critical-bias coupling lock and the d) critical-bias coupling lock with resonant enhancement a variety of different measurement techniques may be used to determine the presence of a trace gas (i.e., a first chemical) in a mass of one or more gases (i.e., two or more chemicals).

For a given measurement setting, the ideal modality may be determined based on the limiting system constraints. For example, in a thermally stable system, the line scanning mode may be combined with critical-bias coupling lock due to minimal duty cycling with control loops depicted in the FIGS. 3(B) and 3(C) and thus provides the highest sensitivity. In cases of large long-term bias-coupling drifts, the line scanning mode may be combined with the critical-bias coupling lock with resonant enhancement, or alternatively, the line locking mode may be combined with the critical-bias coupling lock with resonant enhancement to decouple the effects of coupling bias drift from true trace gas fluctuations.

With reference now once again to FIG. 1, in one embodiment, in one method of operating the system 100, a reference gas is introduced to the reference cell 106. The light source 102, which in this case may be laser light is introduced into the isolator 104 and the coupler 120 which splits the light into a first beam 107 that impinges on a reference gas in the reference cell 106. The second beam 108 which is of a higher power than the first beam 107 is directed to the input waveguide 112B where it couples with the resonator 124 via a coupler 110.

The resonator 124 is filled with the gas sample whose analysis is required. The gas sample generally contains a trace gas (the first chemical) that is present in a mass of another gas (the second chemical, which can itself be a multi-component chemical). The identity of the trace gas may be determined by combining the a) line scanning mode and the b) line locking mode with the c) critical-bias coupling lock and the d) critical-bias coupling lock with resonant enhancement as detailed above.

Figure 4:
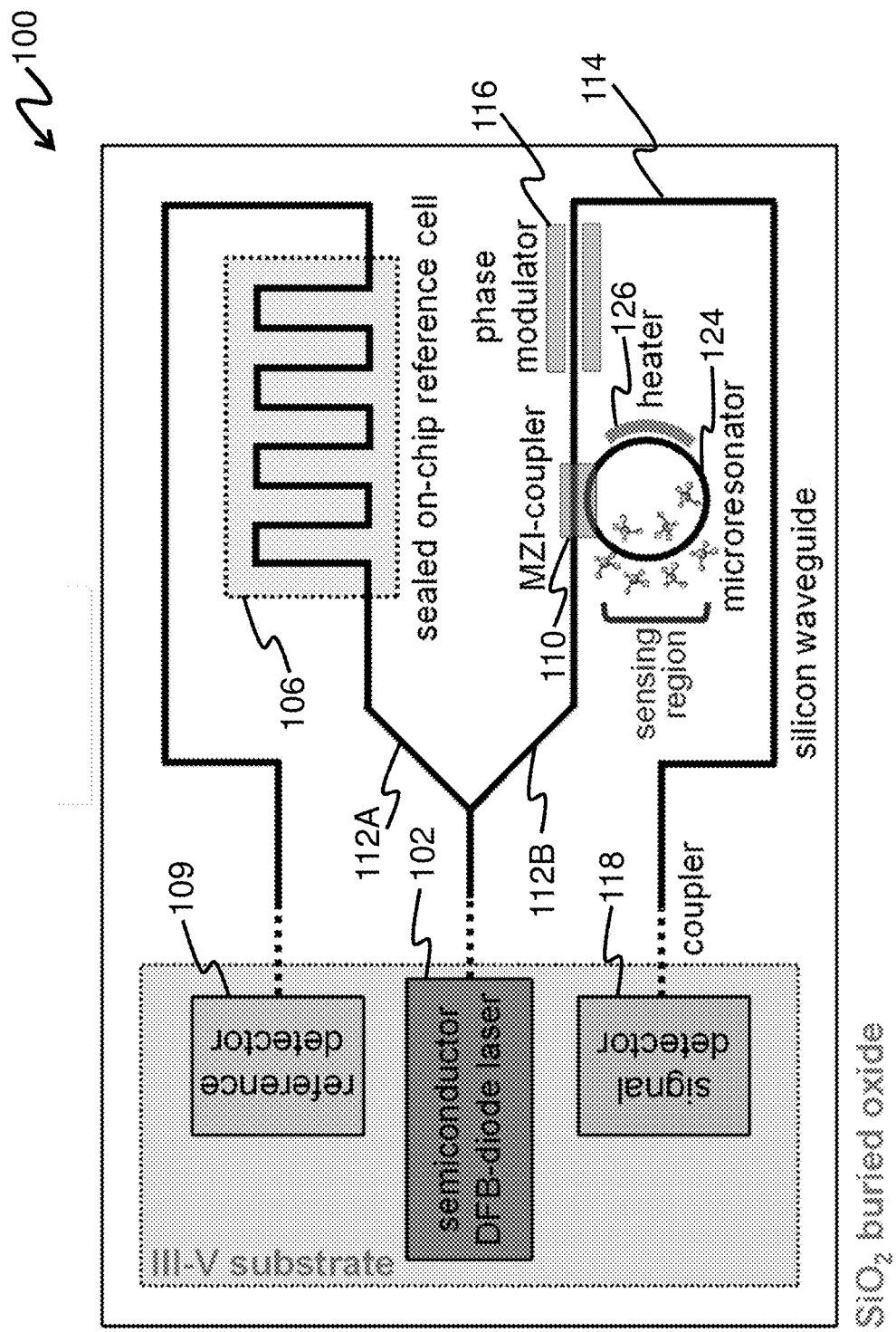
FIG. 4 is an exemplary schematic diagram of a system that is disposed on a chip for detection of trace gases.
Figure 5:
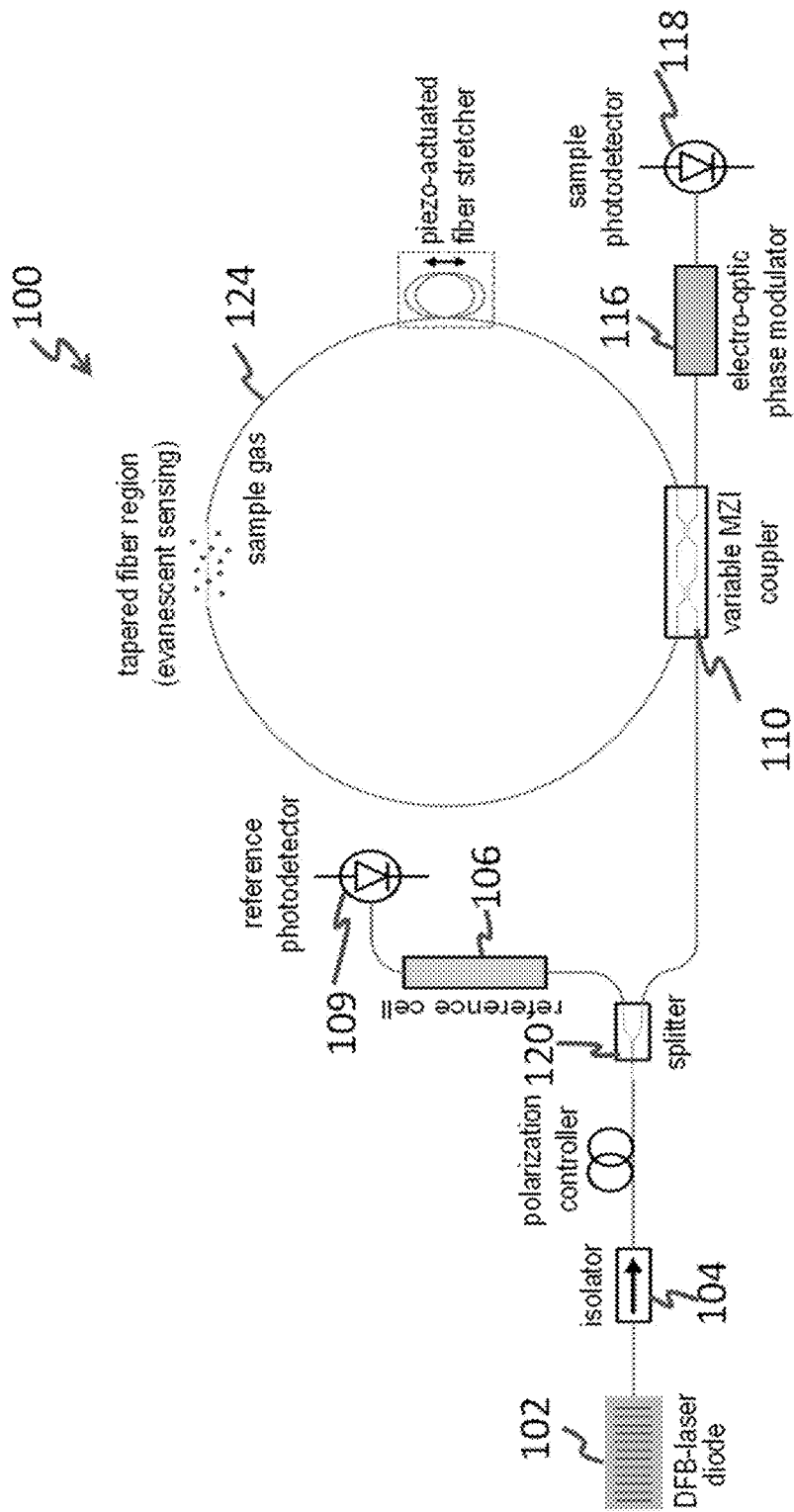
FIG. 5 is an exemplary schematic diagram of a system that comprises a fiber traveling-wave resonator.

In another embodiment, the CMS technique disclosed herein utilizes an on-chip/fiber traveling-wave resonator, shown in FIGS. 4 and 5. Reference numerals and part numbers used in the FIGS. 4 and 5 are similar to those used in the FIGS. 1 and 2. In the on-chip embodiment, coupling modulation is enabled by an on-chip Mach-Zehnder interferometer and electro-optic phase modulation 116 at the output is accomplished using a p-i-n diode junction across the waveguide. A p-i-n diode is a p-n junction with a doping profile tailored so that an intrinsic layer, the "i region" is sandwiched between a p layer and an n layer. A micro-ring resonator 124 is integrated with a MZI coupler 110 and thermally tuned using on-chip heaters 126. PDH-locking is accomplished by a p-i-n junction for high-frequency electro-optic phase modulation. In an alternative embodiment, electro-optic phase modulation 116 at the output is accomplished using a p-n diode junction across the waveguide, with a doping profile which lacks the intrinsic region to increase the electro-optic phase modulation efficiency within the waveguide.

A near-infrared semiconductor laser source 102 and integrated reference (109)/sample photodetectors (118) are fabricated on a III-V substrate 200, which is bonded to the sensor substrate 200 and coupled into the waveguide (112A, 112B and 114). The long-path reference waveguide is fabricated and hermetically sealed onto the chip. The associated control electronic feedback loops are identical to that shown in FIGS. 2 and 3(A) through 3(C).

In summary, in the "on-chip" embodiment depicted in the FIG. 4, the light source is a distributed feedback laser, the coupler is a Mach-Zehnder interferometric coupler, the resonator is a silicon micro-ring, the reference cell is hermetically sealed and is used for wavelength referencing; and the phase modulator is a p-i-n junction.

FIG. 5 depicts another exemplary embodiment of the system 100 that encompasses an entirely fiber-based traveling-wave resonator. The system 100 utilizes commercially available MZI couplers 110, isolators 104, splitters 120, electro-optic modulators 116 and detectors 109 and 118. By using a fiber ring 124, the narrow free-spectral range requires more careful choice of the PDH locking frequency to avoid coupling-modulated crosstalk between resonant modes. A piezo-actuated fiber stretcher 150 is used to tune the ring resonance.

The sensing region makes use of a tapered-fiber section 152, which may be fabricated using either heat-pulling or hydrofluoric acid etching. Alternatively, a free-space path may be incorporated into the fiber ring 124 for ambient gas sensing. Wavelength tunability may also be accomplished using a long ring path and a tunable fiber-Bragg grating to scan sequentially across closely spaced resonator modes.

Alternative embodiments of CMS involve free-space implementations of interferometers. An example of free-space traveling-wave embodiment utilizes a Fabry-Perot (FP) interferometer with modulation of the mirror reflectivity. The laser center wavelength is biased near the maximum transmission point and PDH-locked to this resonant FP-mode. The frequency modulation is actively controlled such that the sidebands are biased near the point of steepest slope on an adjacent FP-mode, which then allows locking to the $2^{nd}$-harmonic (2f) zero-crossing in the wing via coupling modulation (i.e. cavity Q-switching). Tracking the location of the 2f wing zero-crossing provides a measure of the width of the sideband FP-mode, thus allowing direct measurement of the intracavity optical attenuation (analyte absorption by the Beer-Lambert law). In a manner similar to ring-resonator CMS, the coupling modulation may be time-multiplexed with large and small amplitudes at the fixed bias point to enable resonantly enhanced modulation spectroscopy.

The system and the method disclosed herein is exemplified by the following non-limiting examples.

Example 1

Figure 6A:
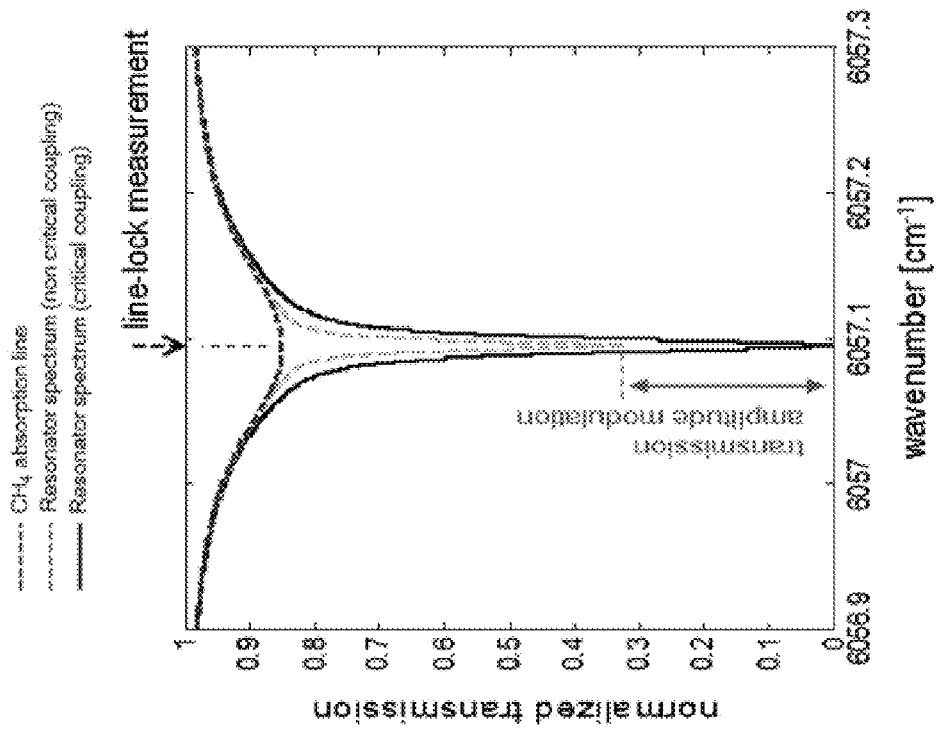
FIG. 6(A) is a graph that shows the transmission of the cavity resonance (black corresponds to critical coupling, grey is off the critical point) superimposed upon a sample (methane) absorption. The coupling modulation (inset) corresponds to a transmittance variation that is measured via phase-sensitive detection.
Figure 6B:
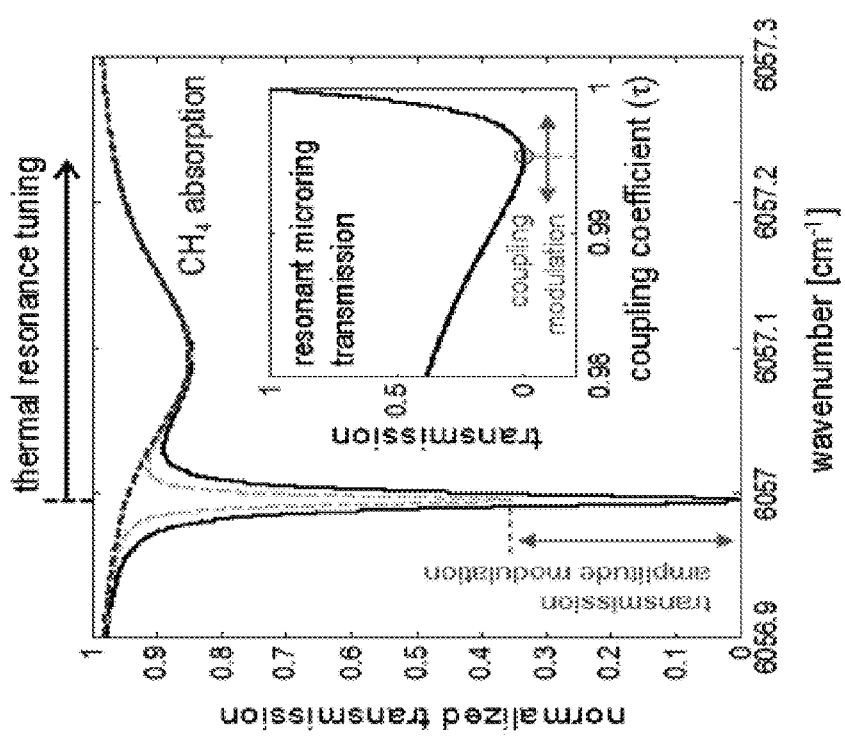
FIG. 6(B) shows the cavity in line-locked mode where the laser, cavity resonance and peak-absorption are locked together for continuous sample measurements.

The FIGS. 6(A) and 6(B) depicts one exemplary method of setting up the resonator for use in the line-locked mode. In this example, in the FIGS. 6(A) and 6(B) transmission of the cavity resonance (black corresponds to critical coupling, grey is off the critical point) superimposed upon a reference sample (methane) absorption. In the FIG. 6(A), the coupling modulation (inset) corresponds to a transmittance variation that is measured via phase-sensitive detection. The laser is PDH-locked to the resonance of the resonator 124 and the resonator 124 cavity is thermally tuned to scan across the absorption transition. FIG. 6(B) shows the cavity in line-locked mode. In line-locked mode, the laser, cavity resonance and peak-absorption are locked together for continuous sample measurements.

It will be understood that when an element or layer is referred to as being "on," "interposed," "disposed," or "between" another element or layer, it can be directly on, interposed, disposed, or between the other element or layer or intervening elements or layers may be present.

It will be understood that, although the terms first, second, third, and the like may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, first element, component, region, layer or section discussed below could be termed second element, component, region, layer or section without departing from the teachings of the present invention.

As used herein, the singular forms "a," "an" and "the" are intended to comprise the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Furthermore, in describing the arrangement of components in embodiments of the present disclosure, the terms "upstream" and "downstream" are used. These terms have their ordinary meaning. For example, an "upstream" device as used herein refers to a device producing a fluid output stream that is fed to a "downstream" device. Moreover, the "downstream" device is the device receiving the output from the "upstream" device. However, it will be apparent to those skilled in the art that a device may be both "upstream" and "downstream" of the same device in certain configurations, e.g., a system comprising a recycle loop.

While the invention has been described with reference to some embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A system for detecting the presence of a trace chemical in a sample comprising:
    a laser light source for generating a beam of light;
    a beam splitter that is operative to split the beam of light into a first beam of light and a second beam of light;
    a reference cell and a first recording device that are operative to receive the first beam of light; where the first recording device is downstream of the reference cell;
    a resonator that is operative to receive the second beam of light via a tunable coupler; where the resonator contains the sample that contains the trace chemical;
    a phase modulator and a second recording device that lie downstream of the resonator and are operative to receive the second beam of light; where the coupler is operative to:
    a) modulate coupling strength between the resonator and an input waveguide; and
    b) biasing a coupling between the coupler and the resonator at a critical point; and
    where an output from the first recording device is compared with an output from the second recording device to determine an amount of the trace chemical.

2. The system of claim 1, where the resonator operates at a wavelength of 100 nanometers to 100 micrometers and where resonance in the resonator is enhanced by time-multiplexing between small amplitude and large amplitude coupling modulation; and where the small amplitude modulation enables lock-in bias at the critical point and large amplitude modulation probes an under-coupled regime.

3. The system of claim 1, where the system uses a feedback control scheme to synchronize wavelengths between the beam of light, resonance in the resonator, and absorption wavelength of a reference gas in the reference cell.

4. The system of claim 1, where the phase modulator further locks a center frequency of the laser beam to a resonance frequency of the resonator via Pound-Drever-Hall locking.

5. The system of claim 1, where the first recording device is a photodiode and where the second recording device is a photodiode.

6. The system of claim 1, where a first feedback control loop uses phase modulation information from the phase modulator and phase-sensitive detection information from the second recording device to lock a central frequency of the laser light source to a resonant frequency of the resonator.

7. The system of claim 1, where a second feedback control loop uses phase-sensitive detection information from the second recording device and coupling modulation information from the coupler to determine critical bias coupling between the coupler and the resonator.

8. The system of claim 1, where a reference-gas feedback bias from the reference cell is coupled with phase-sensitive detection information obtained from the second recording device to lock the laser center wavelength to a reference gas resonance.

9. The system of claim 1, where reference gas feedback bias from the reference cell is combined with Pound-Drever-Hall feedback from the second recording device and the phase modulator to determine how much current is supplied to a thin film heater which is in communication with the resonator.

10. The system of claim 1, where a second feedback control loop that uses phase-sensitive detection information from the second recording device and coupling modulation information from the coupler is used in combination with the first feedback control loop.

11. The system of claim 1, where a a) first feedback control loop that uses phase modulation information obtained from the phase modulator and phase-sensitive detection information obtained from the second recording device is used in combination with a c) reference-gas feedback bias obtained from the reference cell and phase-sensitive detection information obtained from the second recording device; or, where the a) first feedback control loop that uses phase modulation information from the phase modulator and phase-sensitive detection information from the second recording device is used in combination with d) reference gas feedback bias obtained from the reference cell and Pound-Drever-Hall feedback obtained from the second recording device and the phase modulator.

12. The system of claim 1, where a b) second feedback control loop that uses phase-sensitive detection information from the second recording device and coupling modulation information from the coupler is combined with a c) reference-gas feedback bias obtained from the reference cell and phase-sensitive detection information obtained from the second recording device; or, where the b) second feedback control loop that uses phase-sensitive detection information from the second recording device and coupling modulation information from the coupler is used in combination with d) reference gas feedback bias from the reference cell and Pound-Drever-Hall feedback from the second recording device and the phase modulator.

13. The system of claim 1, where a a) first feedback control loop that uses phase modulation information obtained from the phase modulator and phase-sensitive detection information obtained from the second recording device and a b) second feedback control loop that uses phase-sensitive detection information from the second recording device and coupling modulation information from the coupler are used in combination with a c) reference-gas feedback bias obtained from the reference cell and phase-sensitive detection information obtained from the second recording device; and d) reference gas feedback bias obtained from the reference cell and Pound-Drever-Hall feedback obtained from the second recording device and the phase modulator; and where c) and d) are used intermittently to ensure that resonator thermal bias is coarsely centered on an absorption line of interest, while current to the light source is varied to enable a full spectral sweep of a resonance characteristic of the resonator.

14. The system of claim 1, where a a) first feedback control loop that uses phase modulation information obtained from the phase modulator and phase-sensitive detection information obtained from the second recording device and a b) second feedback control loop that uses phase-sensitive detection information from the second recording device and coupling modulation information from the coupler are used in combination with a c) reference-gas feedback bias obtained from the reference cell and phase-sensitive detection information obtained from the second recording device; and d) reference gas feedback bias obtained from the reference cell and Pound-Drever-Hall feedback obtained from the second recording device and the phase modulator; and where c) and d) are used intermittently to ensure that resonator thermal bias is coarsely centered on an absorption line of interest, while the feedback loops a) and b) are simultaneously used and time-multiplexed with feedback control loops of the c) and d) to ensure that resonator frequency and an absorption line of a gas present in the resonator are wavelength-synchronized.

15. The system of claim 1, where the system is disposed on an integrated circuit chip, where:
the light source is a distributed feedback laser;
the coupler is a Mach-Zehnder interferometric coupler;
the resonator comprises a silicon micro-ring;
the reference cell is hermetically sealed and is used for wavelength referencing; and
the phase modulator is a p-i-n diode junction.

16. The system of claim 1, where the resonator is a travelling wave resonator with a tapered portion for evanescent sensing of the chemical and where a piezo-actuated fiber stretcher is used to tune ring resonance.

17. The system of claim 1, where the beam of light has a wavelength in the visible, ultraviolet, near infrared or mid infrared region.

18. A method for determining concentration of a chemical in a sample comprising:
splitting an incident beam of light into a first beam of light and a second beam of light;
transmitting the first beam of light to a reference cell and a first recording device that is operative to receive the first beam of light; where the first recording device is downstream of the reference cell;
transmitting the second beam of light to a phase modulator and a second recording device via a resonator and a coupler; where the resonator contains the sample that contains the chemical;
where the coupler is operative to:
a) modulate coupling strength between the resonator and an input waveguide; and
b) biasing a coupling between the coupler and the resonator at a critical point; and
comparing an output from the second recording device to that of the first recording device to determine an amount of the trace gas.

19. The method of claim 18, further comprising combining information received from a) first feedback control loop that uses phase modulation information obtained from the phase modulator and phase-sensitive detection information obtained from the second recording device and b) second feedback control loop that uses phase-sensitive detection information obtained from the second recording device and coupling modulation information from the coupler are used in combination with information received from a c) reference-gas feedback bias obtained from the reference cell and phase-sensitive detection information obtained from the second recording device; and d) reference gas feedback bias obtained from the reference cell and Pound-Drever-Hall feedback obtained from the second recording device and the phase modulator; and where c) and d) are used intermittently to ensure that resonator thermal bias is coarsely centered on an absorption line of interest, while current to the light source is varied to enable a full spectral sweep of a resonance characteristic of the resonator.

20. The system of claim 1, further comprising combining information obtained from a) first feedback control loop that uses phase modulation information obtained from the phase modulator and phase-sensitive detection information obtained from the second recording device and a b) second feedback control loop that uses phase-sensitive detection information from the second recording device and coupling modulation information from the coupler are used in combination with information obtained from a c) reference-gas feedback bias obtained from the reference cell and phase-sensitive detection information obtained from the second recording device; and d) reference gas feedback bias obtained from the reference cell and Pound-Drever-Hall feedback obtained from the second recording device and the phase modulator; and where c) and d) are used intermittently to ensure that resonator thermal bias is coarsely centered on an absorption line of interest, while the feedback loops a) and b) are simultaneously used and time-multiplexed with feedback control loops of the c) and d) to ensure that resonator frequency and an absorption line of a gas present in the resonator are wavelength-synchronized.

* * * * *